(12) United States Patent
Taylor

(10) Patent No.: US 10,888,245 B2
(45) Date of Patent: Jan. 12, 2021

(54) FAT BURNING MONITORING

(71) Applicant: 1625986 ONTARIO LIMITED, Mount Brydges (CA)

(72) Inventor: Geoffrey Locke Taylor, Winnipeg (CA)

(73) Assignee: Ontario Limited, Ontario (CA)

( * ) Notice: Subject to any disclaimer, the term of this patent is extended or adjusted under 35 U.S.C. 154(b) by 43 days.

(21) Appl. No.: 16/348,231

(22) PCT Filed: Nov. 14, 2017

(86) PCT No.: PCT/CA2017/051353
§ 371 (c)(1),
(2) Date: May 8, 2019

(87) PCT Pub. No.: WO2018/085944
PCT Pub. Date: May 17, 2018

(65) Prior Publication Data
US 2019/0320935 A1    Oct. 24, 2019

Related U.S. Application Data

(60) Provisional application No. 62/420,878, filed on Nov. 11, 2016.

(51) Int. Cl.
*A61B 5/053* (2006.01)
*A61B 5/00* (2006.01)

(52) U.S. Cl.
CPC .......... *A61B 5/0531* (2013.01); *A61B 5/4866* (2013.01); *A61B 5/4872* (2013.01)

(58) Field of Classification Search
CPC ..... A61B 5/681; A61B 5/0031; A61B 5/0095; A61B 5/0531; A61B 5/4866; A61B 5/4872; G06F 19/00
See application file for complete search history.

(56) References Cited

U.S. PATENT DOCUMENTS

| | | | |
|---|---|---|---|
| 2004/0167418 A1* | 8/2004 | Nguyen | G06F 19/00 600/513 |
| 2005/0113650 A1* | 5/2005 | Pacione | A61B 5/4809 600/300 |
| 2008/0161657 A1* | 7/2008 | Bullens | A61B 5/0031 600/301 |
| 2015/0031964 A1* | 1/2015 | Bly | A61B 5/681 600/301 |
| 2015/0051473 A1* | 2/2015 | Huang | A61B 5/0095 600/407 |
| 2016/0120460 A1 | 5/2016 | Eom | |

FOREIGN PATENT DOCUMENTS

| JP | 2001104270 | 4/2001 |
|---|---|---|
| WO | 217061783 | 4/2017 |

* cited by examiner

*Primary Examiner* — Patrick Fernandes
(74) *Attorney, Agent, or Firm* — Michael R Williams; Kyle R Satterthwaite; Ade & Company Inc.

(57) ABSTRACT

An apparatus and a method of monitoring fat burning in a subject non-invasively by measuring electric conductivity or resistance on the skin.

20 Claims, 2 Drawing Sheets

FAT BURNING MONITORING

The instant application is a 371 of PCT Application PCT CA2017/051353, filed Nov. 14, 2017, now abandoned, which claimed the benefit of U.S. Provisional Patent Application, filed Nov. 11, 2016, Ser. No. 62/420,878, now abandoned, and entitled 'FAT BURNING MONITORING", the contents of which are incorporated herein by reference.

BACKGROUND OF THE INVENTION

Currently just over a third of men are overweight or obese, and nearly 40% of women are (Ng M, Fleming T, Robinson M et al. Global, regional and national prevalence of overweight and obesity in children and adults during 1980-2013: A systematic analysis for the Global Burden of Disease Study 2013. Lancet 2014; 384 (9945); 766-81).

Once considered a high-income country problem, overweight and obesity are now on the rise in low- and middle-income countries, particularly in urban settings. These countries are now facing a "double burden" of disease. While they continue to deal with the problems of infectious disease and under-nutrition, they are experiencing a rapid upsurge in non-communicable disease risk factors such as obesity and overweight. In developing countries with emerging economies (classified by the World Bank as lower- and middle-income countries) the rate of increase of childhood overweight and obesity has been more than 30% higher than that of the developed countries, and overweight and obesity are linked to more deaths worldwide than underweight. For example, 65% of the world's population live in countries where overweight and obesity kill more people than underweight (this includes all high-income and most middle-income countries).

The causes of obesity are as varied as the people it affects. At its most basic, of course, obesity results when an energy imbalance occurs due to a difference in calories consumed and calories expended. The body stores these excess calories as body fat, and over time the extra pounds add up. Eat fewer calories than the body burns, weight goes down. This equation can be deceptively simple, though, because it does not account for the multitude of factors that affect what we eat, how much we exercise, and how our bodies process all this energy.

The health consequences associated with overweight and obesity are numerous and at the rate they are progressing the economic burdens will begin to cripple many countries in the near future. For example, 44% is attributed to the diabetes burden, 23% of the heart disease burden and between 7% and 41% of certain cancer burdens are attributable to overweight and obesity.

The following are the major risks: breathing disorders (e.g., sleep apnea, chronic obstructive pulmonary disease); certain types of cancers (e.g., prostate and bowel cancer in men, breast and uterine cancer in women); coronary artery (heart) disease; depression; diabetes; gallbladder or liver disease; gastro esophageal reflux disease (GERO); high blood pressure; high cholesterol; joint disease (e.g., osteoarthritis); stroke.

Aside from the medical complications, obesity is also linked to psychosocial problems such as low self-esteem, discrimination, difficulty finding employment, and reduced quality of life, thus leading to depression, eating disorders and crash diets.

There are hundreds of diets, diet aids, supplements and vitamins, exercise and lifestyle experts located all over the world that are trying to help eradicate this global epidemic.

However what seems to be such a simple concept of eat less and exercise more will equate to weigh less and be healthy does not seem to be achievable for the general masses of the world.

Weight obesity and its causes have, in many ways, become woven into the fabric of our society. To successfully disentangle them will take a multifaceted approach that not only gives individuals the skills to make healthier choices but also sets in place policy and infrastructure that support those choices.

Although the health risks are modifiable or preventable there are very little efforts in progress in the majority of the developing world to control them. We believe there needs to be a simple device to measure and achieve weight management to reduce the economic burden of the disease worldwide.

Cells break down or burn carbohydrates, amino acids and fats to generate ATP, the universal energy currency of cells. In mammals adipose tissue is the major storage site for fat. Ketones are produced when the body burns fats stored in adipose tissue for energy or fuel. They are also produced when there is not enough insulin to help the body use sugar for energy. Without enough insulin, glucose builds up in the blood. Normally, the body gets the energy it needs from carbohydrate in the diet. But stored fat is broken down and ketones are made if the diet does not contain enough carbohydrate to supply the body with sugar (glucose) for energy or if your body can't use blood sugar (glucose) properly.

The excretion of ketone bodies in urine is very low and undetectable by routine urine tests (Rothera's test). However, when the rate of synthesis of ketone bodies exceeds the rate of utilization, their concentration in blood increases; this is known as ketonemia. This is followed by ketonuria—excretion of ketone bodies in urine. The overall picture of ketonemia and ketonuria is commonly referred as ketosis. Being in a state of ketosis is associated with the fat burning metabolic process (Attia, P., "Description of Ketosis"). Smell of acetone in breath is a common feature in ketosis. The occurrence of high levels of ketone bodies in the blood during starvation, a low carbohydrate diet, prolonged heavy exercise and uncontrolled type 1 diabetes mellitus is known as ketosis, and in its extreme form in out-of-control type 1 diabetes mellitus, as ketoacidosis.

When a type 1 diabetic suffers a biological stress event (sepsis, heart attack, infection) or fails to administer enough insulin they may suffer the pathological condition ketoacidosis. Liver cells increase metabolism of fatty acids into ketones in an attempt to supply energy to peripheral cells which are unable to transport glucose in the absence of insulin. The resulting very high levels of blood glucose and ketone bodies lower the pH of the blood and trigger the kidneys to attempt to excrete the glucose and ketones. Osmotic diuresis of glucose will cause further removal of water and electrolytes from the blood resulting in potentially fatal dehydration, tachycardia and hypotension.

The Ketone Bodies

Ketone body metabolism is highly regulated and circulating levels of ketone bodies are determined by their rates of production and utilization. Ketone production is aggressively suppressed by glucose. As glucose stores become depleted ketone body production increases. In humans, basal serum concentration of β-hydroxybutyrate is in the low micromolar range, gradually increasing to 1-2 mM after 2 days of fasting and 6-8 mM with prolonged starvation. Ninety minutes of intense exercise can also cause β-hydroxybutyrate concentration to increase to 1-2 mM while uncontrolled diabetics can have -hydroxybutyrate concentrations of 25 mM.

Individuals who follow a low-carbohydrate diet will also develop ketosis, sometimes called nutritional ketosis, but the level of ketone body concentrations are on the order of 0.5-5 mM whereas the pathological ketoacidosis is 15-25 mM.

As the mainstream diet of diabetic patients is so high in carbohydrate, ketosis is rarely seen without ketoacidosis resulting from low serum insulin levels.

Measurement of Ketone in Blood

A blood test analyzed by a laboratory is the most accurate method of measuring ketones. However, laboratories' tests are not practical for people following a diet, or for prompt testing.

"In-house", current methods for measuring levels of ketones in blood include urine strips, or invasive devices (pricking of your finger). Not only are these two methods extremely expensive, not widely known or talked about, but also they are not globally available.

U.S. Pat. No. 8,871,521 ("US •521") discloses a breath ketone detector. Although non-invasive, this device has many disadvantages. Diabetic ketoacidosis is characterized by the accumulation of ketone bodies in blood, however, this device allegedly measures ketone bodies in breath and, therefore, it represents an indirect measure of blood ketones. The device is disposable, i.e. designed for one-time use, which means that a user in need must make sure to have an unused device available at all times. The device has an expiry date at ambient, which means that a user in need cannot keep too large a stock of devices. The operation of the device may not be suitable for most users; indeed, according to US '521 a user must "take a deep breath and blow for 30 seconds through the end of the tube designated by arrow. Blow very hard. Exhale through the tube, Do not inhale."

U.S. Pat. No. 9,456,749 discloses a portable device having an integrated chemical sensor sensitive to ketones within a breath sample. This device is incapable of registering electric conductivity of the skin or the breath.

US20090054799 discloses a sensor with a breath delivery system with the breath sensor capable of detecting an analyte in the breath, including acetone. Breath activates the breath sensor resulting in an electrical signal that is transmitted to portable electronic device.

US20160331272 discloses a portable device for measuring acetone in breath using a nanoparticle-based sensor. This document teaches that electrical aspects of the breath measurement devices pose risks as electrostatic discharges can occur that may impact the device.

Other prior art documents include: US20160371590, WO2016192941, U.S. Pat. No. 8,453,601, US20150073290

None of the devices of the prior art measure surface conductivity or conductivity due to breath condensates (neither of which is a gas) nor a correlation between the surface or breath conductivity and ketosis.

As can be seen, the range of technologies suitable for non-invasive, repeated, in-vivo measurement of blood ketones is rather limited. A suitable technology needs to be sensitive to blood chemistry, ideally not require the addition of reagents in order to make the measurement and present no hazard to the patient or operator. Technologies that potentially meet these requirements include UV-Vis, mid infrared, near infrared, Raman and Terahertz (far infrared) spectroscopy. However, ketone bodies are small molecules, and it is not possible to get a reliable measurement of ketone bodies across an intact skin.

Cardiovascular machines such as treadmills, stationary bikes, elliptical trainers, stair steppers, to name a few, come with a variety of widgets that let the user measure his/her heart rate and calculate the approximate amounts of calories being burnt. However, neither heart rate nor calories burnt may represent that the person is burning fat. Regarding calories, exercise requires energy, and this energy is measured using calories. The source for energy may come from either fat or muscle glycogen. As the body adapts to each exercise, it becomes more efficient in its use of calories, therefore burning less. The amount of muscle also has an impact on calories burned. Because muscle is metabolically active—more muscle means more calories being burned. The so called "fat burning zone" may be calculated by using the resting heart rate (RHR), the maximum heart rate (MHR), and the heart rate reserve (HRR) as follows: Fat burning range=RHR+HRR×0.5. However, this relationship may depend on the level of fitness of the person and his/her age. Therefore, a cardiovascular machine that more accurately measures when a person is actually fat burning, is needed. None of the currently used devices for measuring ketone levels may be adapted for exercise machines.

Presented herein are devices and methods that let users see firsthand what the treatments, foods or exercises that are available to them are doing to their own personal metabolism and the burning of fat in their bodies, and how they can take control and monitor their own personal success by self-empowerment. It should be understood that the applicants are not advocating or intending to enable unsafe, unsupervised extreme dieting, but rather taking the view that the diets have to be properly constituted and that people following these diets should be under medical supervision.

SUMMARY OF THE INVENTION

The present invention relates, in one embodiment, to an apparatus and method of monitoring fat-burning in a subject.

In one embodiment, the present invention relates to an apparatus for monitoring fat burning in a subject non-invasively, the apparatus having means for measuring an electric conductivity of the skin of a subject, and at least one out-put signal configured to turn on when the electric conductivity of the skin is in a high mega ohm range indicative of the subject not burning fat.

In another embodiment of the apparatus of the previous embodiment, the apparatus further comprises another out-put signal that turns on when the electric conductivity of the skin of the subject is in a low mega ohm range, indicative of the subject burning fat.

In one embodiment, the present invention is an ohm meter for monitoring fat burning in a subject. The ohm meter, in one embodiment, includes: (i) an interdigitated portion having two opposing ends and configured for contacting a skin of the subject and measure surface conductivity of the subject's skin; (ii) a ketosis signal that turns on when the conductivity of the skin is in a high mega ohm range indicative of the subject not burning fat, the ketosis signal being connected to one end of the interdigitated portion and (iii) a power source.

In another embodiment, the ohm meter of the present invention further includes non-ketosis signal that turns on when the skin conductivity is in a high mega ohm range indicative of the subject not burning fat, the second signal being connected to the other end of the interdigitated portion.

In another embodiment, the ohm meter of the present invention further includes an intermediate signal that turns one when the conductivity of the skin in an intermediate range between the low mega ohm range and the high mega ohm range, wherein the third signal is indicative of an intermediate state of ketosis.

In one embodiment, the present invention relates to a method for monitoring fat burning in a subject non-invasively, the method comprising measuring an electric conductivity on the skin of a subject, wherein when the electric conductivity of the skin is in a low mega ohm range indicative of the subject burning fat.

In another embodiment, the present invention is a method of monitoring fat burning in a subject, the method comprising: (a) providing the ohm meter of any of the previous embodiments, (b) pressing the interdigitated portion against skin of the subject, wherein the ketosis signal being turned on is indicative of the subject burning fat.

DESCRIPTION OF THE PREFERRED EMBODIMENTS

Figure 1:
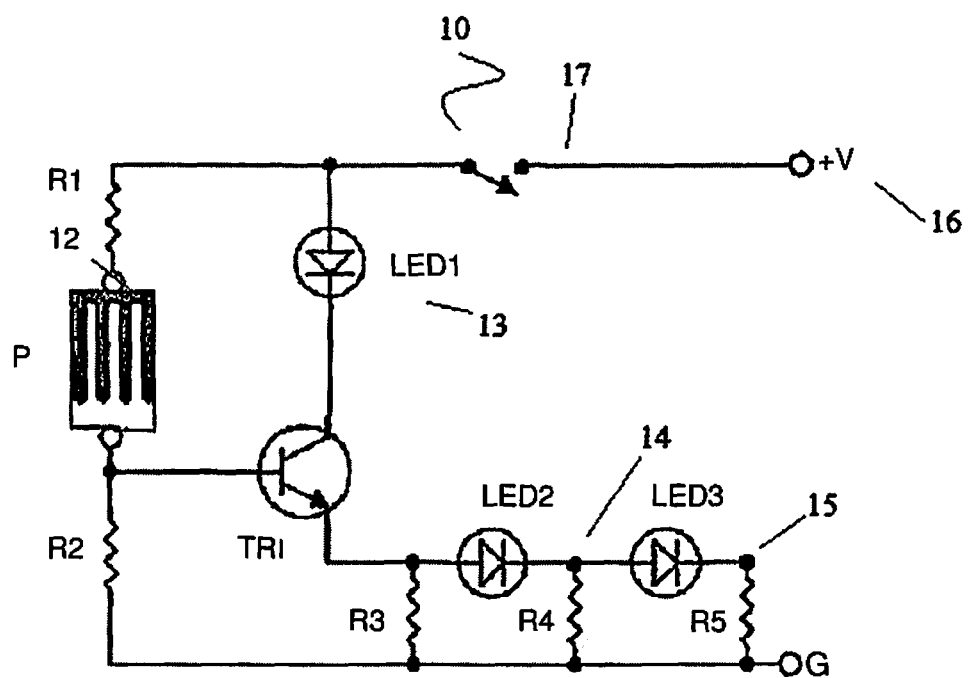
FIG. 1 shows a circuit diagram of an ohm meter for monitoring fat burning in accordance to one embodiment of the present invention.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Definitions

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise. In order to aid in the understanding and preparation of the within invention, the following illustrative, non-limiting, examples are provided.

"Ketone body" refers to molecules that are produced by the liver from fatty acids during periods of low food intake (fasting) or carbohydrate restriction for cells of the body to use as energy instead of glucose. Examples of ketone bodies include acetone, acetoacetic acid, and beta-hydroxybutyric acid.

In this document, the term "fat-burning molecules" refers to one or more molecules whose presence or absence in blood or whose presence in blood at or above a normal threshold is indicative of stored fats burning. Non-limiting examples of fat-burning molecules include acetone, acetoacetic acid, and beta-hydroxybutyric acid, insulin, glucagon, free fatty acids and glycerol.

Subject includes any mammal, including humans.

Overview

The present invention relates to methods and devices for the non-invasive monitoring fat burning in a subject.

Acetone is a normal metabolite and its presence in breath levels ranges from a relatively high 0.5 ppmv for healthy individuals to hundreds of ppmv for critically ill, ketoacidotic diabetics. Acetone readily equilibrates throughout the body and can also be detected emanating from the skin. Acetone emitted from the skin correlate directly with blood beta-hydroxybutyrate. This has been confirmed by using gas chromatography.

Skin acetone concentrations of persons with diabetes (about 188±17 ppb) are significantly higher than normal subjects (about 87±10 ppb). Skin acetone concentrations are related to blood beta-hydroxybutyrate, blood glucose and HbA1c in patients with diabetes. Skin acetone concentration is high (approx. 940 ppb) in a patient with diabetic ketoacidosis, and drops to approximately 80 ppb after insulin therapy.

Skin acetone is herein used as a screening test for ketosis and of diabetic control and of ketone production in diabetes and other ketogenic conditions.

In one embodiment, the present invention is an apparatus or device to indicate fat burning by measuring skin conductance. In another embodiment, the present invention is a method to indicate fat burning by measuring skin impedance.

Acetone is more conductive than salts that are naturally occurring in the skin. Conductivity of acetone is about 0.02 µS/cm. The conductivity of sweat is about 0.0002 µS/cm (although the conductivity of sweat is higher for people with Cystic Fibrosis). Given that acetone is hydrophobic, it may help separate the influence of salts naturally occurring on the skin.

As will be apparent to one of skill in the art, the siemens (symbol: S) is the derived unit of electric conductance, electric susceptance and electric admittance in the International System of Units (SI). Conductance, susceptance, and admittance are the reciprocals of resistance, reactance, and impedance respectively; hence one siemens is redundantly equal to the reciprocal of one ohm.

(Note: Acetone has a CAS Registry No.: 67-64-1 and has these other names: 2-Propanone, Dimethyl ketone, Propanone). Three molecules are grouped together as "ketone bodies", acetoacetate, -hydroxybutyrate and acetone.

As discussed herein, the device is an apparatus for non-invasively monitoring ketosis. Ketosis can be used as an indication that a subject is burning fat. As such, the device is an apparatus for monitoring fat-burning in a subject.

The apparatus has means for measuring an electric conductivity of the skin of a subject, and at least one out-put signal configured to turn on when the electric conductivity of the skin is in a high mega ohm range indicative of the subject burning fat and another (optional) out-put signal that turns on when the electric conductivity of the skin of the subject is in a low mega ohm range indicative of the subject not burning fat.

The apparatus is an ohm meter, which includes: (i) an interdigitated portion having at least two opposing ends and configured for contacting a skin of the subject and measure surface conductivity of the subject's skin; (ii) a ketosis signal that turns on when the conductivity of the skin is in a high mega ohm range indicative of the subject burning fat, the ketosis signal being connected to one end of the interdigitated portion and (iii) a power source.

Specifically, the movement of acetone to the skin surface results in higher skin conductivity and this movement of acetone is indicative of fat burning. Typically, this increase in conductivity is about an order of magnitude, but will of course depend on the normal skin conductivity of the individual and exactly how much acetone has moved to the skin surface. For example, an individual may have a skin conductivity of about 0.2 µS when not in ketosis but have a skin conductivity of about 0.02 µS when in ketosis or burning fat.

It is also important to note that the transition to ketosis happens over a relatively short period of time such as for example 20-30 minutes.

As such, the apparatus can effectively measure the sweat on the skin of the individual for non-invasively measuring ketosis.

Also disclosed is a method for monitoring fat burning in a subject non-invasively, the method including the steps of measuring an electric conductivity of the skin of a subject, wherein when the electric conductivity of the skin is in a low mega ohm range indicative of the subject burning fat. As discussed above, the low mega ohm range may be a decrease by about an order of magnitude over the electric conductivity of the skin when the subject is not burning fat.

For example, a comparison of conductances may be measured by two different oscillators (i.e. depth profiling the changes in conductance), thereby enabling measurement of the migration of acetone to the skin. In other words, it is possible to measure the gradient of the acetone concentrations as the acetone makes its way to the surface of the skin. For example, the first derivative of any one depth or the comparison of two depths indicates the flow rate and thereby indicates whether acetone levels are increasing or decreasing.

As will be appreciated by one of skill in the art, shorter frequencies of oscillation will obtain measurements that are closer to the skin surface while longer frequencies will obtain measurements from deeper in the tissue.

While this may be done with two different oscillators, in some embodiments, a single oscillator arranged to function at two or more frequencies, for example, a scanning oscillator, may be used in the device.

Alternatively, a single oscillator may be used for measurements. In these embodiments, measurements may be obtained by varying one or more of the frequency of oscillation, the phase or phase shift and the amplitude while keeping at least one of the other measurements constant.

Thus, the device and the method effectively provide a ketosis signal that is turned on when conductivity of the subcutaneous tissue below the skin changes as the subject's metabolism changes to a state in which fat is being burned, that is, acetone is being produced and/or moved to the surface of the skin.

As discussed herein, subcutaneous impedance may be measured by a variety of means, for example by using a temperature-compensated oscillator or comparing two matched oscillators, wherein one is in closer proximity to the skin. As discussed above, the ability to compare surface to sub-surface impedance allows the measurement of a spatial gradient of acetone.

In one particular aspect of the method, the electric conductivity of the skin is measured using one of the above described apparatuses.

The device is an apparatus for non-invasively ketosis. Ketosis can be used as an indication that a subject is burning fat. As such, the device is an apparatus for monitoring fat-burning in a subject.

The apparatus has means for measuring an electric conductivity of the skin or breath of a subject and at least one out-put signal configured to turn on when the electric conductivity of the skin or breath is in a high mega ohm range indicative of the subject burning fat and another (optional) out-put signal that turns on when the electric conductivity of the skin or breath of the subject is in a low mega ohm range, indicative of the subject not burning fat.

The apparatus is an ohm meter, which includes: (i) an interdigitated portion comprising close proximity conductors (preferably indium tin oxide or a non-oxidizing. Metallic, although any suitable conductor may be used) and having two opposing ends and the interdigitated portion being configured for contacting a skin of the subject or configured for receiving breath from the subject and measure surface conductivity of the subject's skin or the conductivity of the skin; (ii) a ketosis signal that turns on when the conductivity of the skin is in a high mega ohm range indicative of the subject burning fat, the ketosis signal being connected to one end of the interdigitated portion and (iii) a power source.

Ketometer

Alternatively, the apparatus can measure surface or sub-surface impedance with an oscillator, which includes: (i) an interdigitated portion comprising close proximity conductors (preferably indium tin oxide or a non-oxidizing. Metallic, although any suitable conductor may be used) and having two opposing ends and the interdigitated portion being configured for contacting a skin of the subject or configured for receiving breath from the subject and measure surface conductivity of the subject's skin or the conductivity of the skin; (ii) a ketosis signal that turns on when the conductivity of the skin is in a low mega ohm range indicative of the subject burning fat, the ketosis signal being connected to one end of the interdigitated portion and (iii) a power source.

As discussed herein, in these embodiments, this device will have a pair of matched frequency oscillators, one near and aimed at but not in direct contact with the skin and a second matching oscillator aimed away from the skin. The difference between these two gives an indication of the conductance of the skin while reducing the temperature drift normally experienced. For example, by varying the frequency of the oscillator pair from a few hertz (under 10) to approximately 20 MHz will provide depth profile information about the surface and subsurface conductance. The comparison between the two readings of the conductance at two skin depths provides information about an acetone gradient, as discussed above.

In some embodiments, the device is arranged to be worn on the wrist. Readings may be taken every minute or so and the readings recorded/stored together with a time stamp. The device would have the ability to extract the readings to review the data and allow us to look for changes in conductance or ideally indicate significant changes in conductivity by illuminating a series of green LEDs. That is, in some embodiments, the illumination of LEDs around the outside of the device either in terms of number or brightness may be increased as conductance increases and conversely reducing the numbers and/or intensity when the conductance drops.

As discussed herein, the method is based largely on an increase in conductance of approximately an order of magnitude, not specifically for an absolute value of conductivity, although suitable values are provided as a guide for one of skill in the art.

In some embodiments, the device may be arranged with the ability to initially null the frequency difference between the two oscillators after installation on the wrist. Future changes would give the influence of acetone and other things that influence conductance in the oscillator aimed at the skin.

As will be appreciated by one of skill in the art, temperature drift will be the same for both oscillators and should have a minimal influence on the readings.

Given the fact that we do not need the absolute value of conductance, the following represent suitable ranges for functioning devices:

i. Sensitivity; 0.25 us (micro siemens)
ii. Range; 0 to 10 us
iii. Accuracy; =/−0.25 us
iv. Precision; 0.25 us In some embodiments, data is used to develop a curve to map/identify the conductance changes as experience is gained about when the person goes in and out of ketosis.

In some embodiments, a secondary resistance comparison is made using an AC (for example, 8 Hz) three-way interdigitated surface contact. This would take advantage of the surface acoustic wave properties (SAW) since these are also influenced by changes to the mechanical properties of the tissue and these will change as acetone levels build up. In some embodiments, this would be a three-way interdigitated contact sensor as shown in FIG. 2.

Figure 2:
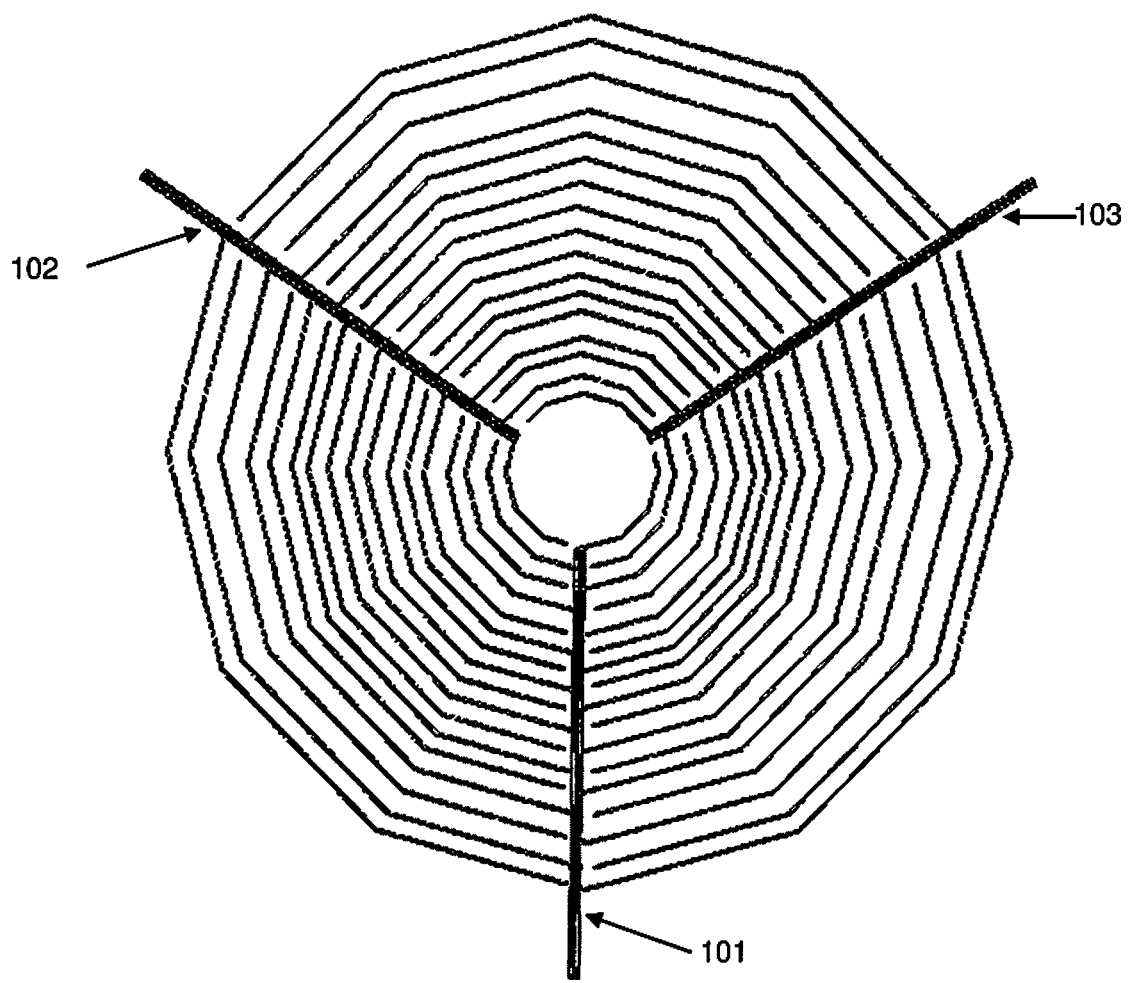
FIG. 2 is a schematic diagram of a three-way interdigitated contact sensor.

Specifically, shown in FIG. 2 are three separate conductive strips, labelled as 101, 102 and 103. As can be seen in FIG. 2, each conductive strip has traces that pass between the other two strips. The close proximity of the strips allows for accurate measurements of the conductance and impedance between the adjacent strips and allows for comparisons between the relative readings, thereby reducing polarization errors (for example, 101-102, 101-103, 102-103, 103-101, 103-102 and 102-101). It is further of note that in those embodiments wherein direct resistance is measured, the conductive strips may not be coated; however, in those embodiments wherein oscillators are used, the conductive strips may be coated.

The apparatus can measure the sweat on the skin of the individual or in the breath of the individual for non-invasively measuring ketosis.

Also disclosed is a method for monitoring fat burning in a subject non-invasively, the method including the steps of measuring an electric conductivity of the skin or breath of a subject, wherein when the electric conductivity of the skin or breath is in a low mega ohm range, that is indicative of the subject burning fat.

In one particular aspect of the method, the electric conductivity of the skin is measured using one of the above described apparatuses.

The device is an apparatus for non-invasively detecting whether a person is in a state of ketosis. Ketosis can be used as an indication that the subject is burning fat. As such, the device is an apparatus for monitoring fat-burning in a subject.

The apparatus has means for measuring an electric conductivity of the skin or breath of a subject, and at least one out-put signal configured to turn on when the electric conductivity of the skin or breath is in a high low mega ohm range indicative of the subject burning fat and another (optional) out-put signal that turns on when the electric conductivity of the skin or breath of the subject is in a low high mega ohm range, indicative of the subject not burning fat.

The Device

In accordance with one embodiment, the invention uses skin conductance to differentiate between ranges of conductivity as a screening test for ketosis.

A resistance measurement of the surface conductance can be made with an ohm meter however the resistance is in the multi megaohm range and special provisions must be made to adapt a comparative instrument, to allow it to detect the desired resistances.

FIG. 1 illustrates an embodiment of a circuit diagram of the ohm meter of the present invention.

With reference to FIG. 1, electrical contacts (P) section 12 of the ohm meter 10 where the skin conductance/resistances are to be measured, are fitted preferably with an indium tin oxide (ITO) coated plastic skin contact sheet. The P section 12 may also be referred to as the interdigitated area 12. The plastic sheet is etched to form an interdigitated labyrinth of the appropriate special frequency to achieve the desired resistance ranges such that the relatively high resistance measured during normal metabolic states can be differentiated from the more conductive states associated with being in ketosis and indicated by the sequential illumination of the LED1 13, LED2 14, and LED3 15. LED1-LED3 13-15 may take the form of light-emitting diode lamps. The general skin conductivity of individuals may vary. Varying the spatial frequency of the interdigitated contact area changes the resistance range and allows the device to be selectively matched to users with different base line conductivities. In one embodiment, the spatial frequency of the interdigitated area is approximately 1 to 2 per mm. In another embodiment, the spatial frequency of the interdigitated area is equal or greater than 2 per mm.

The contact area 12 may also be interdigitated, electrically separated, stainless (or other non-corroding, coated conductor) wires. ITO coated plastic skin contact sheet is preferred because of its affinity to acetone. The interdigitated contact area may be made of stainless steel or individual wires coated to prevent corrosion, or an exposed coated printed circuit board or foil. In another embodiment the contact area may be a single use contact surface. This would eliminate any complications that may arise due to surface cleaning or degradation of the contact area.

LED1 13 is also referred to as the non-ketosis signal, LED2 14 is also referred to as the intermediate state of ketosis signal, and LED3 15 is also referred to as the ketosis signal. LED1 13, LED2 14 and LED3 15 may take any colour. For example, LED1 13 may be green, LED2 14 may be yellow and LED3 15 may be red. If only the green LED1 13 lights up, the person being tested is not in ketosis. If the LED2 14 yellow illuminates (although in some embodiments, both LED1 13 and LED2 14 illuminate) the person is in an intermediate state. If LED3 15 red illuminates or alternatively in another embodiment, all three LEDS are illuminated, the person is in ketosis. With the referenced circuit of FIG. 1, LED2 and LED3 will never light up alone, i.e. LED I alone (no ketosis), LED1 and LED2 (intermediate state) or LED1, LED2 and LED3 (ketosis).

A power supply section 16 of the meter 10 may be of any suitable type and is illustrated in the form of four 1.5V button cells, LR44 or equivalent. In another embodiment the supplied voltage is alternating current in the high M Hz range. This concentrates the current flow on the surface of the skin to further differentiate skin conductivity to subcutaneous conductivity.

In another embodiment of the present invention the device includes both DC and AC. In this embodiment the current flow difference measured across the contact area using DC and AC is compared. This contrasts the contributions to conductivity that comes from the subcutaneous path, to that of the surface conductivity.

The ohm meter 10 is operative when the electrical contact section 12 is in contact with a subject's skin. Upon contact with the skin, a voltage is formed along resistances R1-R5. A transistor TR1, which is connected to the negative side of the electrical contact 12, which along with resistances R2-R5 form a voltage divider network which allows transistor TR1 to progressively light the lights LED1 13, LED2 14 and LED3 15.

The resisters R1-R5 may be generic resisters. For example, R1=1 k ohm, R2=12K ohm R3=2 K ohm R4=1K ohm R5=680 ohm. However, as will be apparent to one of skill in the art, other resisters may be used within the scope of the invention.

The transistor TR1 may be a basic power transistor TRIC 458, but it could be a 828 OR 1959 OR 1815 or 945 or 1740.

The system includes an on off (momentary) switch 17. The switch, in one embodiment, may be placed on the contact surface 12 so that when a user presses the device onto the skin it triggered the switch.

The device of the present invention, in another embodiment, includes processing means and it may also include a memory module.

The processing means may be a programmable processor included to execute program instructions to guide a data process module to directly store captured data into the memory module, to initiate data upload from the memory module to a computing means via data upload module, to manage energy usage and so forth.

The memory module may include any appropriate type of memory now known or later developed including without limitation, read-only memory (ROM), random access memory (RAM), flash memory, and a set of registers included within the programmable processor.

In one embodiment, the processing means may take the form of a microprocessor such as the Maxim Health Sensor Platform MASXREFDES100#. Maxim MAXREFDES100# health sensor platform is an integrated sensor platform that helps customers evaluate Maxim's complex and innovative medical and high-end fitness solutions. The platform integrates one biopotential analog front-end solution (MAX30003), one pulse oximeter and heart-rate sensor (MAX30101), two human body temperature sensors (MAX30205), one 3-axis accelerometer, one 3D accelerometer and 3D gyroscope, and one absolute barometric pressure sensor. As will be apparent to one of skill in the art, in other embodiments, other suitable processing means may also be used.

In another embodiment, the device of the present invention may include wireless communication capabilities that would allow it to connect with a computing device, such as a laptop, a desk top, wireless devices such as cellular phones and pads, or to directly connect to the Internet. The information stored in the memory means may be downloaded into a computing device for storage or for further analysis.

With reference to FIG. 1, the contact area (in this case the ITO area 12) is pressed onto an appropriate area of a user's skin such as the inside of the wrist or inside tip (fingerprint area) of a finger. The switch 17 is momentarily pressed to allow current flow and the degree of ketosis is indicated by the illumination of the LEDs.

If the person is following a program to achieve ketosis such as fasting or dieting, the LED indication informs the user whether they are in a fat burning state or not.

The device of the present invention may be used on any part of the body. The top of the fingertip is a site particularly well suited for performing skin conductivity. The inside of the forearm is yet another particularly well suited part for performing skin conductivity with the device of the present invention. The ear lobe is yet another site particularly well suited for performing skin conductivity.

In operation, with reference to FIG. 1, the interdigitated area is pressed into contact with-the skin of a subject, for example the index finger or the inside of the forearm. This measures the surface conductivity of the skin. If LED1 13 only lights up the subject is not in ketosis (i.e. not burning fat). If LED1 13 and LED2 14 are illuminated (or just LED2 14) the subject is in an intermediate state. If LED1-LED3 13-15 are illuminated (or just LED3 15) the subject is in ketosis, i.e. fat burning.

Without further elaboration, it is believed that one of ordinary skill in the art can, based on the description presented herein, utilize the present invention to the full extent. All publications cited are incorporated by reference.

Future applications claiming priority to this application may or may not include the following claims, and may include claims broader, narrower, or entirely different from the following claims.

The scope of the claims should not be limited by the preferred embodiments set forth in the examples but should be given the broadest interpretation consistent with the description as a whole.

The invention claimed is:

1. A method for non-invasively detecting if a subject is in ketosis and burning fat comprising:
   providing a device comprising:
   an interdigitated portion configured for measuring impedance of skin surface of the subject, said interdigitated portion having at least two separate electrical contacts configured for detecting movement of acetone to the skin surface, said movement of acetone being indicative of the subject being in ketosis and burning fat;
   a power source; and
   a ketosis signal connected to one end of the interdigitated portion, said ketosis signal configured to be activated when the impedance of the skin surface of the subject decreases by approximately an order of magnitude compared to impedance of the skin surface of the subject when not in ketosis,
   placing the device on a body of the subject such that said at least two electrical contacts of said interdigitated portion are contacting the skin surface of the subject;
   said device detecting movement of acetone to the skin surface by measuring the impedance of the skin surface of the subject; and
   said device activating the ketosis signal when the impedance of the skin surface of the subject has decreased by approximately an order of magnitude compared to the impedance of the skin surface of the subject when not in ketosis.

2. The method as claimed in claim 1 wherein the device further comprises a second signal configured to activate when the impedance of the skin surface of the subject is approximately the impedance of the skin surface of the subject when not in ketosis.

3. The method as claimed in claim 1 wherein the device further comprises a force sensor operationally coupled to the interdigitated portion, the force sensor generating a signal that is representative of a status of fat burning.

4. The method as claimed in claim 1 wherein the device further comprises a processor coupled to the interdigitated portion.

5. The method as claimed in claim 4 wherein the device further comprises a memory module coupled to the processor.

6. The method as claimed in claim 5 wherein the device further comprises a housing that is sized and shaped to couple the interdigitated portion of the device to a body of the subject.

7. The method as claimed in claim 1 wherein the interdigitated portion comprises a first interdigitated conductor strip and a second interdigitated conductor strip, the first interdigitated conductor strip and the second interdigitated conductor strip separated by a third interdigitated conductor strip for measuring a difference in impedance between the first interdigitated conductor strip and the second interdigitated conductor strip.

8. The method as claimed in claim 7, wherein the first interdigitated conductor strip measures impedance of the skin surface of the subject and the second interdigitated conductor strip measures a reference impedance of air adjacent to the subject.

9. The method as claimed in claim 7 wherein the first interdigitated conductor strip is a first oscillator and the second interdigitated conductor strip is a second oscillator.

10. The method as claimed in claim 1 wherein the impedance in a low mega ohm range indicates that the subject is in ketosis.

11. The method as claimed in claim 1 wherein conductance in a high mega ohm range indicates that the subject is in ketosis.

12. A device for non-invasively detecting if a subject is in ketosis and burning fat comprising:
an interdigitated portion configured for measuring impedance of skin surface of the subject, said interdigitated portion having at least two separate electrical contacts;
said at least two electrical contacts of said interdigitated portion configured for contacting the skin surface of the subject and detecting movement of acetone to the skin surface, said movement of acetone being indicative of the subject being in ketosis and burning fat;
a power source; and
a ketosis signal connected to one end of the interdigitated portion, said ketosis signal configured for activation when the impedance of the skin surface of the subject decreases by approximately an order of magnitude compared to impedance of the skin surface of the subject when not in ketosis.

13. The device as claimed in claim 12 wherein the device further comprises a second signal arranged configured for activation when the impedance of the skin surface of the subject is approximately the impedance of the skin surface of the subject when not in ketosis.

14. The device as claimed in claim 12 wherein the device further comprises a force sensor operationally coupled to the interdigitated portion.

15. The device as claimed in claim 12 wherein the device further comprises a processor coupled to the interdigitated portion.

16. The device as claimed in claim 15 wherein the device further comprises a memory module coupled to the processor.

17. The device as claimed in claim 16 wherein the device further comprises a housing that is sized and shaped to couple the interdigitated portion of the device to a body of the subject, a force sensor, the processor and the memory module being located in the housing.

18. The device as claimed in claim 12 wherein the interdigitated portion comprises a first interdigitated conductor strip and a second interdigitated conductor strip, the first interdigitated conductor strip and the second interdigitated conductor strip separated by a third interdigitated conductor strip for measuring a difference in impedance between the first interdigitated conductor strip and the second interdigitated conductor strip.

19. The device as claimed in claim 18, wherein the first interdigitated conductor strip is arranged for measuring the impedance of the skin surface of the subject and the second interdigitated conductor strip is arranged for measuring a reference impedance of air adjacent to the subject.

20. The device as claimed in claim 18 wherein the first interdigitated conductor strip is a first oscillator and the second interdigitated conductor strip is a second oscillator.

* * * * *